United States Patent [19]

Takayanagi et al.

[11] Patent Number: 4,765,983
[45] Date of Patent: Aug. 23, 1988

[54] ADHESIVE MEDICAL TAPES FOR ORAL MUCOSA

[75] Inventors: Hitoshi Takayanagi; Yoshihiro Sawai, both of Toyama, Japan

[73] Assignee: Yamanouchi Pharmaceutical Co., Ltd., Tokyo, Japan

[21] Appl. No.: 869,186

[22] Filed: May 30, 1986

[30] Foreign Application Priority Data

Jun. 5, 1985 [JP] Japan .................................. 60-121849

[51] Int. Cl.$^4$ .............................................. A61F 13/00
[52] U.S. Cl. .................................... 424/434; 424/435; 424/449
[58] Field of Search ................. 424/435, 448, 449

[56] References Cited

U.S. PATENT DOCUMENTS

| 4,291,015 | 9/1981 | Keith et al. | 424/435 |
| 4,307,075 | 12/1981 | Martin | 424/435 |
| 4,517,173 | 5/1985 | Kizawa | 424/435 |
| 4,531,914 | 7/1985 | Spinello | 424/435 |
| 4,568,536 | 2/1986 | Kronenthal et al. | 424/435 |
| 4,594,240 | 6/1986 | Kawata et al. | 424/435 |
| 4,597,960 | 8/1986 | Cohen | 424/435 |

Primary Examiner—Thurman K. Page
Assistant Examiner—L. R. Horne
Attorney, Agent, or Firm—Burgess, Ryan & Wayne

[57] ABSTRACT

Adhesive medical tapes for oral mucosa comprising a support layer composed of an intestine-soluble polymer and a medicament-containing layer composed of a water-soluble polymer containing at least one kind of a steroid or non-steroid antiphlogistic and analgesic medicament.

6 Claims, 6 Drawing Sheets

ADHESIVE MEDICAL TAPES FOR ORAL MUCOSA

FIELD OF THE INVENTION

This invention relates to an adhesive medical tape for oral mucosa which gives an antiphlogistic and analgesic qualities when applied to affected parts in the oral cavity. More particularly, the invention relates to an adhesive medical tape for oral mucosa comprising a support layer composed of an intestine-soluble polymer and a medicament-containing layer composed of a water-soluble polymer containing at least one kind of a steroid or nonsteroid antiphlogistic and analgesic medicament.

BACKGROUND OF THE INVENTION

Hitherto, for the treatment of, for example, stomatitis, an ointment, a liquid medicine, or a tablet (for adherence) has been used. However, an ointment or a liquid medicament is dissolved in saliva or body temperature in a short period of time after application and swallowed, whereby a long lasting medical effect cannot be expected for these medicaments. Moreover since there is a fluctuation on each application amount in the case of applying the above-described medicament, a dosage of a constant amount is difficult.

On the other hand, a tablet can maintain the medical effect for a long period of time and improve the problem on the fluctuation of the dosage of the medicament but it is difficult to accurately apply the medicament to the affected portion in the oral cavity since the diameter thereof is as small as a few millimeters. Also, since such a tablet has a thickness of a little over 1 mm, it gives an incongruent feeling when applied to a portion in the oral cavity and hence it is not easy to apply a tablet, which sometimes results in detachment of the medicament from the applied portion. Accordingly, a sure medical effect cannot sometimes be expected in the case of the tablet.

As the result of various investigations on the optimum form of an adhesive medicament for this kind of purpose, the inventors have reached conclusions that the medicament must be in a form capable of covering a relatively broad area since an affected part is in an inconvenient position for observing from outside and that the medicament must be in a form of giving an incongruent feeling as less as possible.

It is necessary that the medicament meeting these conditions is a film-form medicament, is eatable, and is soluble in water but these requirements only are insufficient and further the form of medicament must be as thin as possible and must contain a sufficient amount of the medicament.

SUMMARY OF THE INVENTION

The object of this invention is, therefore, to provide a slow releasing adhesive medical tape for oral mucosa which is a film-form adhesive medicament and the medicament-containing layer of which is at least water-soluble and is gradually dissolved to provide the medical effect.

In such an adhesive medical tape for oral mucosa, it is inevitable to uniformly mix, disperse, or dissolve an antiphlogistic and analgesic medicament in a watre-soluble polymer film but the aforesaid object of this invention cannot be attained by only applying or embeding the film. In the case of applying or coating such a medicament, a multilayer structure is required for protecting the film to increase the thickness of the medicament film and also to make the production step complicated. Also, in the case of embeding, the embeded medicament cannot sufficiently cover an affected portion and hence a sufficeint medical effect cannot be expected.

Thus, according to this invention, there is provided an adhesive medical tape for oral mucosa comprising a support layer composed of an intestine-soluble polymer and at least one medicament-containing layer composed of a water-soluble polymer containing at least one kind of an antiphlogistic and analgesic medicament.

DESCRIPTION OF THE PREFERRED EMBODIMENT

Figure 1:
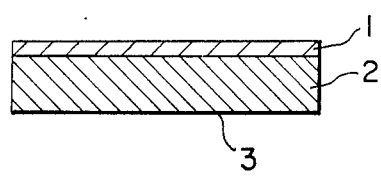
FIG. 1 is an enlarged schematic cross-sectional view showing an embodiment of the adhesive medical tape of this invention having one medicament layer.

A steroid antiphlogistic and analgesic agent generally possess an excellent anti inflammatory activity, can be easily formed into a lasting preparation, and hence can be advantageously used in this invention. As a matter of course, a non-steroid medicament having excellent inflammatory activity can be also used in this invention.

As a steroid medicament, there are triamcinolone acetonide, fluocinolone acetonide, dexamethasone, dexamethasone acetate, hydrocortisone acetate, prednisolone, prednisolone valerate, betamethasone valerate, and be clomethasone propionate, etc. They can be used solely or as a mixture of them. Also, as a non-steroid medicament, there are indomethecin, dichlofenac sodium, bufexamac, ibuprofenpiconol, butyl flufenamate and bendazac and they can be used solely or as a mixture thereof.

The water-soluble polymer constituting the medicament-containing layer in this invention is a polymer capable of dissolving mainly in the oral cavity or stomach and specific examples of such a polymer are polyvinylpyrrolidone (hereafter it is abbreviated as PVP), gelatin, polyvinyl alcohol (PVA), sodium polyacrylate, sodium carboxymethyl cellulose (NaCMC), starch, xanthane gum, karaya gum, sodium alginate, methyl cellulose (MC), carboxyvinyl polymer, agar-agar, hydroxypropyl cellulose [in particular, highly substituted one (HPC-H)], etc. The medicament-containing layer in this invention is mainly composed of one or more of these polymers.

In addition, the water-soluble polymer in this invention also includes a water-swelling polymer such as lowly substituted hydroxypropyl cellulose (HPC-L).

The thickness of the medicament-containing layer composed of the water-soluble polymer and the medicament is determined by considering the dissolving speed thereof, the lasting time of the medicament, and the incongruent feeling. In other words, if the thickness of the layer is too thin, the water-soluble polymer is dissolved too fast although the dissolving speed may differ according to the nature of the polymer and hence the thickness is more than 20 μm, preferably more than 30 μm. On the other hand, the maximum thickness is at most 300 μm, preferably 200 μm although it depends upon individual difference.

The medicament layer may be composed of one layer but is preferably composed of two or more layers. In the case of two layers, the layer (layer II) adhering to a mucous membrane is composed of a fast dissolving layer and other layer (layer I) is composed of a slow dissolving layer to control the dissolution of the medicament layer or the concentration of the medicament in layer II is increased, whereby the adhesive medical tape having a quick acting property and a long lasting property is obtained. Also, by employing a quick dissolving layer as layer II, the initial adhesion of the adhesive medical tape to a mucous membrane is increased. For forming the quick dissolving film layer or the slow dissolving film layer, each layer may be formed by properly selecting the water-soluble polymer according to the expected use.

In this invention, two or more medicaments may be used simultaneously and when the medicament layer is composed of two or more layers, each layer may, as a matter of course, contain each different medicament. It is proper that the proportion of the medicament is about 0.05 to 1.0 part by weight for a steroid medicament and about 0.5 to 5.0 parts by weight for a non-steroid medicament.

As the intestine-soluble polymer (i.e., a polymer which is dissolved in the intestines) constituting the support layer in this invention, there are hydroxypropylmethyl cellulose phthalate (HPMCP), cellulose acetate phthalate (CAP), carboxymethylethyl cellulose (CMEC), poly(methacrylic acid, methylmethacrylate) (e.g., Eudragit L.S., trade name, made by Röhm Pharma GMBH), shellac, etc.

The support layer composed of such an intestine-soluble polymer functions to prevent the form of the adhesive medical tape from being collapsed or deformed and also prevent the face (front face) of the adhesive medical tape opposite the face sticking to a mucous membrane from sticking to other mucous membrane. Also, if the support layer is not formed, the front face side which does not stick to the mucous membrane is also dissolved, whereby the medicament contained in the portion is lost in vain as well as the lasting property thereof is reduced. However, the occurence of these disadvantages is prevented by the formation of the support layer in this invention. It is also clear from FIG. 4 explained herein below that when the support layer is formed, the dissolution of such a portion scarcely occurs (i.e., the useless dissolution is very small). Furthermore, when the support layer is formed on the medicament layer which is composed of two layers for obtaining a quick acting property and long lasting property, the long lasting property thereof can be further increased. It is proper that the thickness of the support layer is about 2 to 20 μm.

When preparing each layer, it is preferable to use softening agent. Propylene glycol, glycerin, polyethylene glycol 400, triacetin, etc. are cited as softening agent. For medicament layer, propylene glycol, glycerin, polyethylene glycol 400, etc. are suitable. And for support layer, propylene glycol, triacetin, etc. are suitable.

The solvent which is used to dissolve the components of medicament layer is not particularly limited but ethanol, water, etc. are suitable. Also, as the solvent which is used to dissolve the components of support layer, organic solvent(s) which can dissolve intestine-soluble polymer is used, but ethanol, methylene chloride, etc. are used preferably.

Adhesive medical tape of this invention are prepared by following manner.

The components of the support layer are dissolved in the organic solvent and the resulting solution is spread on a released paper followed by drying to form a support layer and then a solution which is obtained by dissolving the components of medicament layer in the solvent is spread thereon and dried to form an adhesive medical tape. In case of two medicament layers a solution which is obtained by dissolving the components of the second medicament layer in the solvent is spread on the first medicament layer and dried to form a second medicament layer.

Further, if necessary, a cover film for protecting the medicament layer is used.

In this invention, one or more kinds of steroid or non-steroid antiphlogistic and analgesic medicaments exist in a water-soluble polymer film, with the dissolution of the film in the oral cavity, the medicaments directly act to the affected part in the oral cavity to which the film is adhered. In particular, since the adhesive medical tape of this invention wholly adhere to a mucous membrane in the oral cavity and acts the antiphlogistic and analgesic activity thereof directly to the affected part in the whole adhered area, the adhesive medical tape of this invention has a structural feature of easily adhering to the affected part and also can accurately give the antiphlogistic and analgesic activity to the affected part as compared to the case of tablet or embedding or coating the medicament in a film. In particular, it is a remarkable effect of this invention that the medical effect can be expected immediately after applying the tape. Also, the adhesive medical tape of this invention has good long lasting property.

The adhesive medical tape of this invention is particularly useful for the treatment of stomatitis.

In addition, when the adhesive medical tape of this invention is applied to an affected portion in the oral cavity, the adhesive medical tape of a proper size may be placed on the affected portion so that the tape covers the affected portion (the medicament layer thereof is stuck to the affected portion) by a clean finger or tweezers.

Then, the test method for the dissolution of medicaments and the results thereof are shown below.

(1) Test Method

Figure 3:
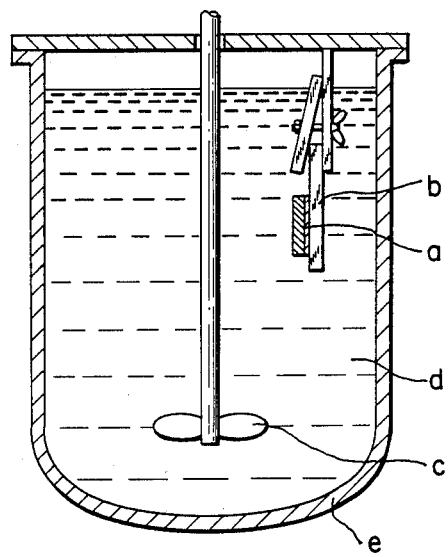
FIG. 3 is a schematic cross-sectional view of a test device used for the dissolution test.

By partially modifying the dissolution test device by the Japan Pharmacopoeia, a dissolution test device for adhesive medical tapes as shown in FIG. 3 was prepared and the dissolution test was performed using the device. As shown in FIG. 3, the test device is composed of a beaker e having a rotary vane c and contains a physiological saline solution d (30° C.). A sample a (3 cm×3 cm) is stuck to a bakerite plate b.

A support layer of a sample was stuck to the bakerite plate of the test device using a double faced adhesive tape and 900 ml of physiological saline solution previously heated to 37° C. was placed in the beaker and stirred. While continuing stirring at 100 r.p.m. at temperature of 37° C.±5° C., 20 ml of the solution was sampled per a definite time, and the same amount of a physiological saline solution was supplied in each time. The absorbance of each sample was measured using a ultraviolet spectrometer and the dissolution rate was calculated.

(2) Result

Figure 4:
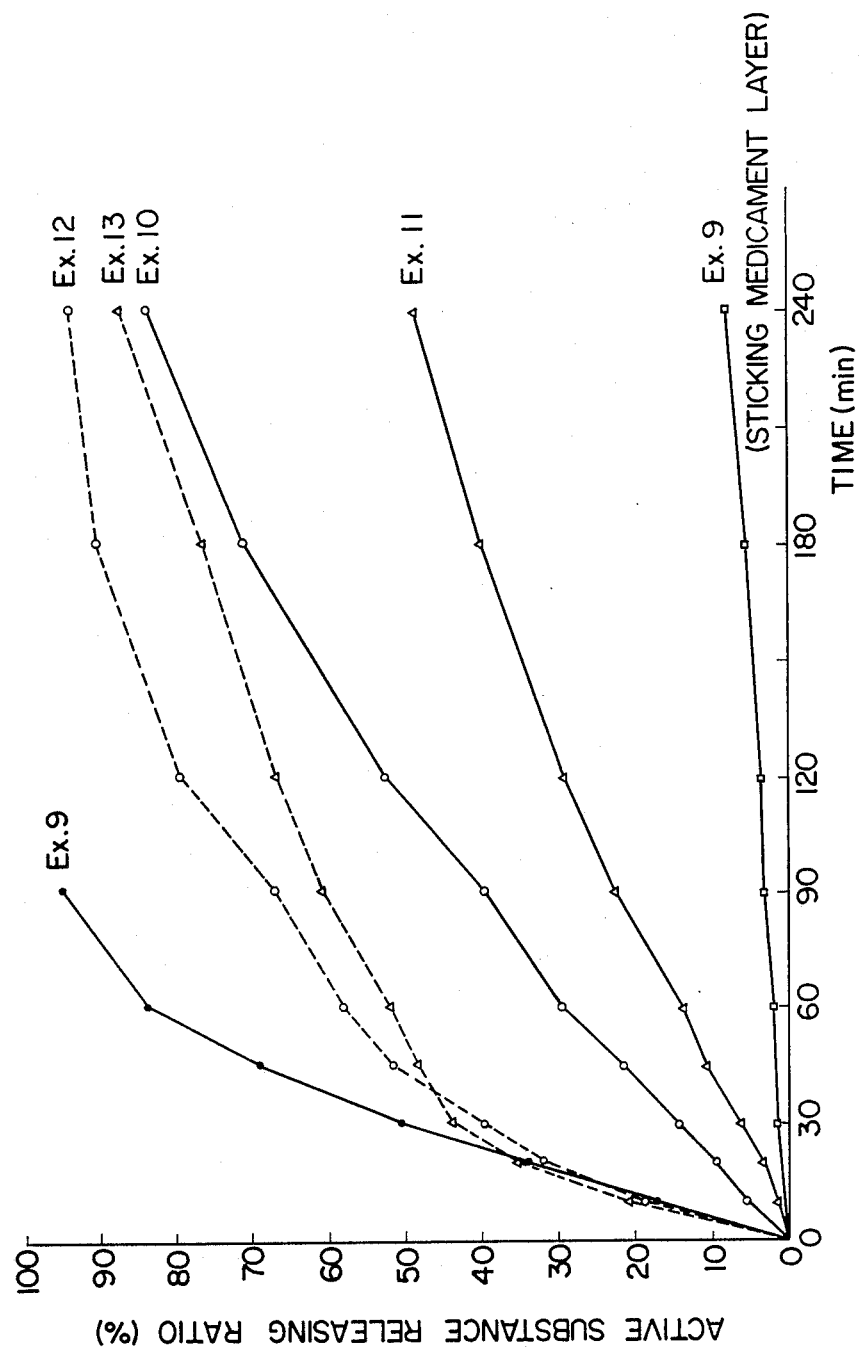
FIG. 4 is a graph showing the active substance releasing ratios of the adhesive medical tapes in Examples 9 to 13.
Figure 5:
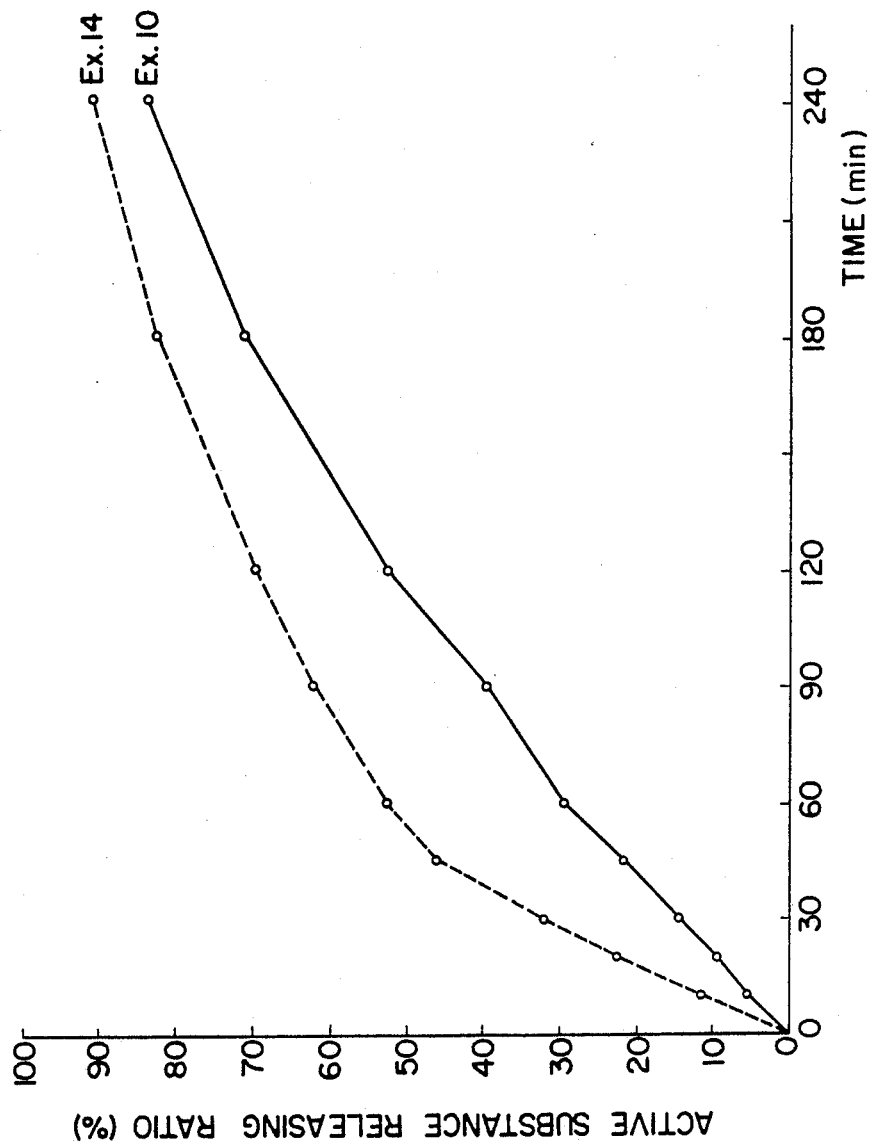
FIG. 5 is a graph showing the active substance releasing ratios of the adhesive medical tapes in Examples 10 and 14.
Figure 6:
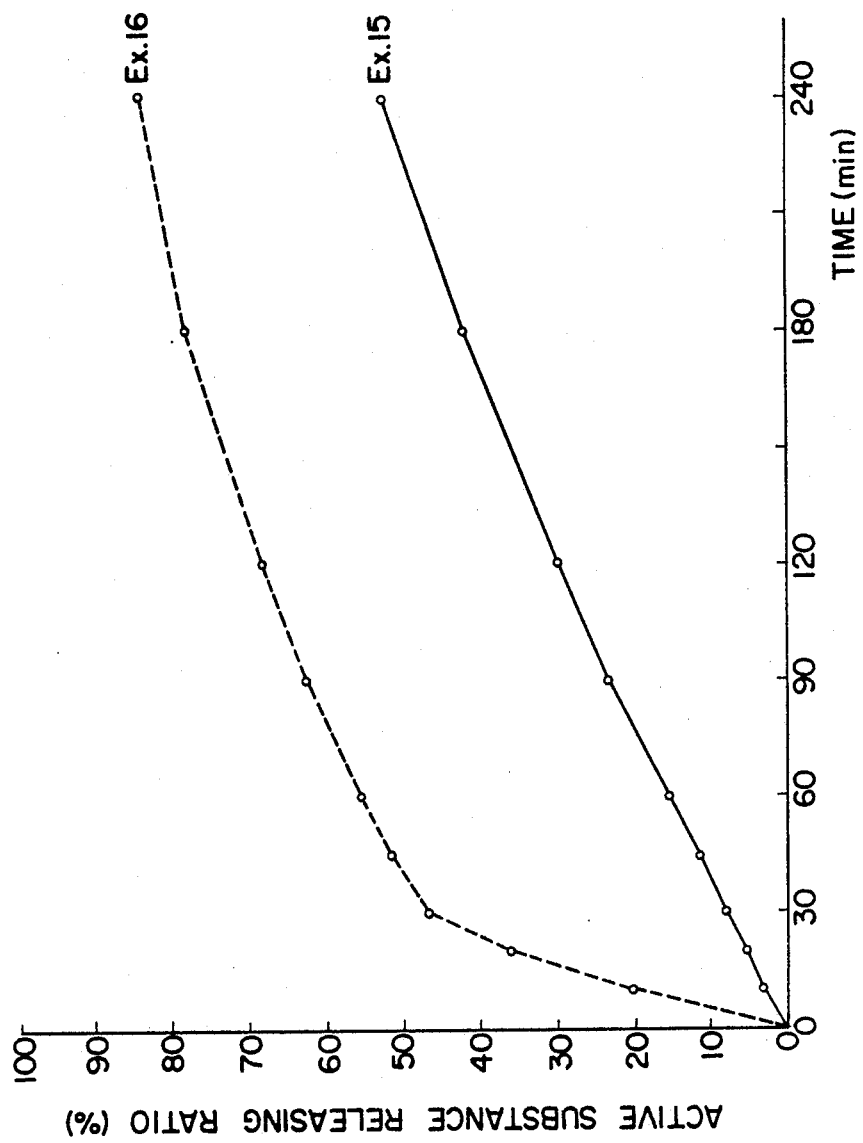
FIG. 6 is a graph showing the active substance releasing ratios of the adhesive medical tapes in Examples 15 and 16.
Figure 7:
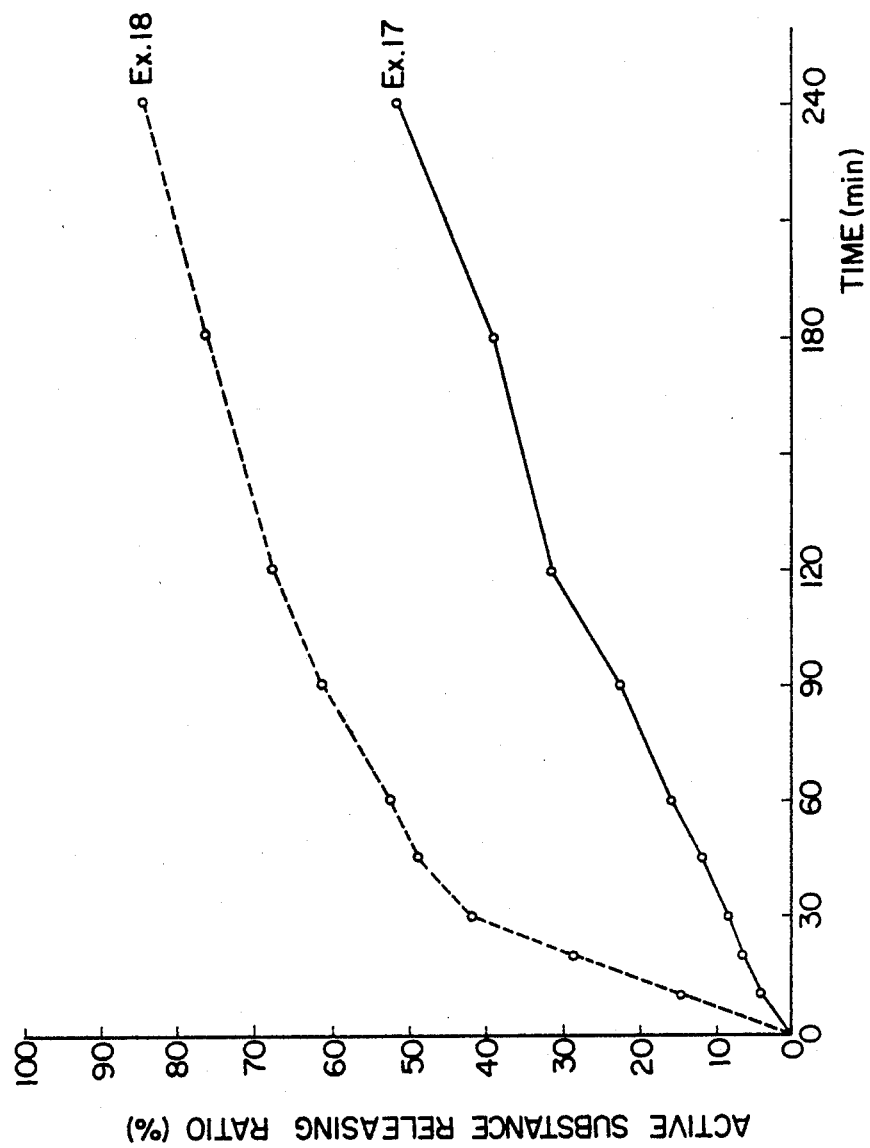
FIG. 7 is a graph showing the active substance releasing ratios of the adhesive medical tapes in Examples 17 and 18.

The results about Examples 9 to 13 (medicament: triamcinolone acetonide) are shown in FIG. 4 of the accompanying drawings. As shown in the figure, since the sample in Example 9 shows a good initial dissolving property, the sample may shows a good quick acting property but the long lasting property thereof is not sufficient.

The samples in Examples 10 and 11 are insufficeint in initial dissolving property and hence they are a little inferior in quick acting property.

The sample of Example 12 is composed of two laminate layers of the layer in Example 9 and the layer in Example 10 and the sample in Example 13 is composed of two laminate layers of the layer in Example 9 and the layer in Example 11 (however, the thickness of each layer in Examples 12 and 13 is ½ of that of the layer in Examples 9, 10, and 11). In these cases, the samples are better in both the initial dissolving property and the long lasting property.

In addition, the same test was performed by sticking the medicament layer (layer II) of the adhesive medical tape in Example 9 to the bakerite plate using a double faced adhesive tape and the result is shown in FIG. 4 by —☐—. As is clear from the result, it can be seen that the adhesive medical tape is scarcely dissolved from the support layer side. In FIG. 4, —●— stands for Example 9, —o— for Example 10, —△— for Example 11, ---●-- for Example 12, and ---△--- for Example 13.

The test results about Examples 10 and 14 (medicament: triamcinolone acetonide), Examples 15 and 16 (medicament: dexamethasone), Examples 17 and 18 (medicament: hydrocortisone acetate), and Examples 19 and 20 (medicament: Indomethacin) are shown in FIG. 5 to FIG. 8.

In any cases, the adhesive medical tapes having double medicament layers are superior in initial dissolving property and better in quick acting property and long lasting property.

Figure 8:
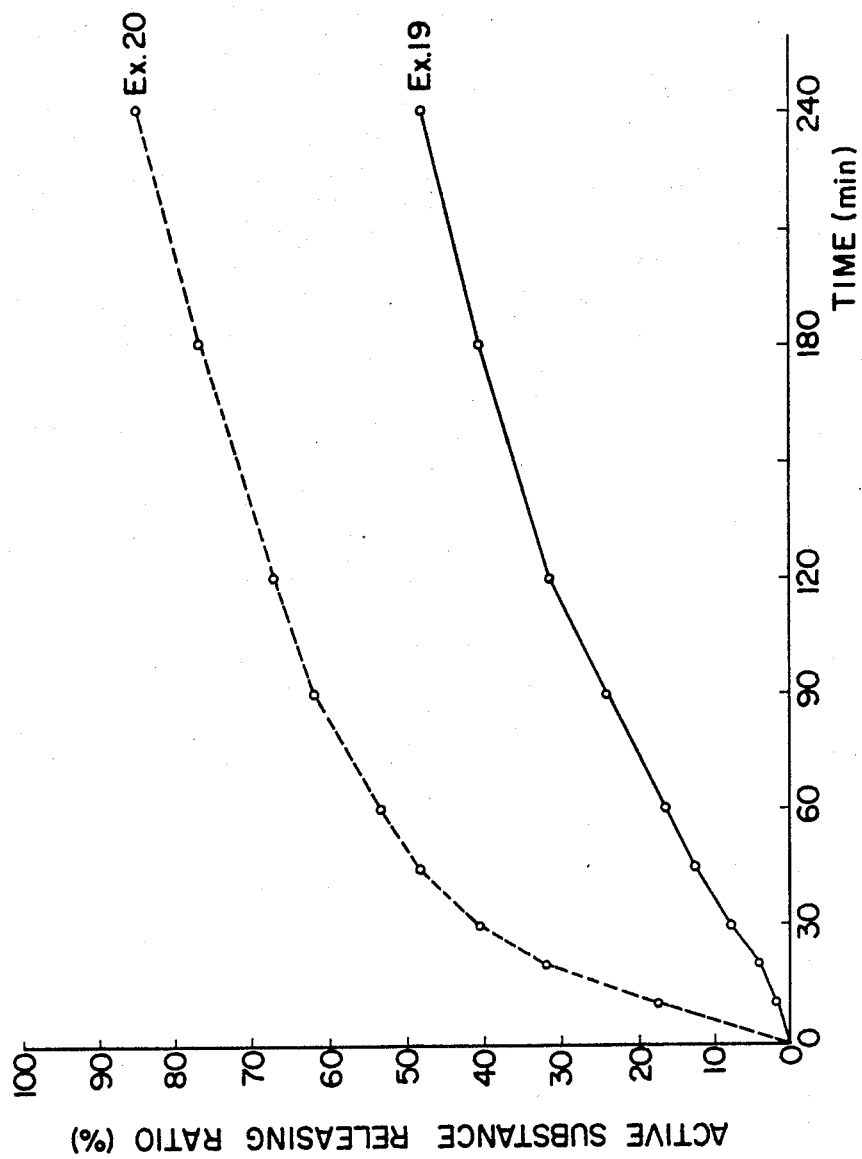
FIG. 8 is a graph showing the active substance releasing ratios of the adhesive medical tapes in Examples 19 and 20.

In these figures, —o— stands for Example 10 (FIG. 5), Example 15 (FIG. 6), Example 17 (FIG. 7), and Example 19 (FIG. 8) and ---o--- stands for Example 14 (FIG. 5), Example 16 (FIG. 6), Example 18 (FIG. 7), and Example 20 (FIG. 8).

Then, the following examples are intended to illustrate this invention but not to limit it in any way.

First, FIG. 1 shows an embodiment of the adhesive medical tape of this invention having one medicament-containing layer composed of support layer 1 and a medicament-containing layer 2. In addition, numeral 3 shows adhesive surface.

Figure 2:
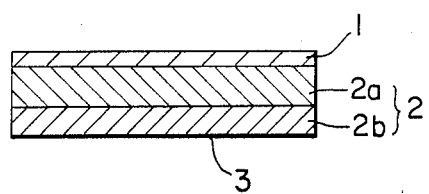
FIG. 2 is an enlarged schematic cross-sectional view showing another embodiment of the adhesive medical tape having two medicament layers.

Also, FIG. 2 shows other embodiment of the adhesive medical tape of this invention having double medicament-containing layers composed of a support layer 1 and a medicament-containing layer 2 which is composed of layer I 2a and layer II 2b. Numeral 3 is also adhesive surface.

EXAMPLE 1

In 1,000 parts by weight of ethanol were dissolved 50 parts by weight of polyvinyl alcohol, 20 parts by weight of highly substituted hydroxypropyl cellulose, and 20 parts by weight of lowly substituted hydroxypropyl cellulose. Also, 0.1 part by weight of triamcinolone acetonide was dissolved in 9.9 parts by weight of propylene glycol under heating. Both the solution was mixed with each other with stirring to provide a homogeneous liquid product. Apart from this, 90 parts by weight of hydroxypropylmethyl cellulose phthalate and 10 parts by weight of triacetin were dispersed in 250 parts by weight of ethanol and after adding thereto 250 parts by weight of methylene chloride, the mixture was stirred to provide a homogeneous liquid for support. Then, the liquid for support was spread on a released paper followed by drying to form a support layer of 20 $\mu$m in thickness and then the above-described liquid product containing triamcinolone acetonide was spread thereon and dried to form a two-layer type adhesive medical tape (having one medicament-containing layer) having a thickness of about 150 $\mu$m.

EXAMPLE 2

In 250 parts by weight of ethanol were dissolved 50 parts by weight of polyvinylpyrrolidone, 9.9 parts by weight of propylene glycol, and 0.1 part by weight of triamcinolone acetonide with stirring. Apart from this, 40 parts by weight of starch was added to 20 parts by weight of water followed by heating. Both solutions were mixed together with stirring to provide a homogeneous liquid. By spreading the liquid on the support layer formed as in Example 1 and drying, an adhesive medical tape of about 150 $\mu$m in thickness was produced.

EXAMPLE 3

By following the same procedure as Example 2 except that 40 parts by weight of gelatin was used in place of starch, an adhesive medical tape was produced. The thickness was about 150 $\mu$m.

EXAMPLE 4

By following the same procedure as Example using 1.0 part by weight of indimethacin as the antiphlogistic and analgesic agent and 9.0 parts by weight of a softening agent, polyethylene glycol 400, an adhesive medical tape of about 150 $\mu$m in thickness was produced.

EXAMPLE 5

By following the same procedure as Example 1 using 1.0 part by weight of diclofenac sodium as an antiphlogistic and analgesic agent, 50 parts by weight of sodium polyacrylate and 40 parts by weight of starch as a film-forming agent, 9,0 parts by weight of glycerol as a softening agent, and 500 parts by weight of water as solvent, an adhesive medical tape of about 150 $\mu$m in thickness was produced.

EXAMPLE 6

By following the same procedure as Example 5 except that 40 parts by weight of gelatin was used in place of starch as the film-forming agent, an adhesive medical tape of about 150 μm in thickness was produced.

EXAMPLE 7

A mixture of 90 parts by weight of hydroxypropylmethyl cellulose phthalate, 10 parts by weight of triacetin, 250 parts by weight of ethanol, and 250 parts by weight of methylene chloride was spread on a released paper and dried to form an intestine-soluble film (support layer) of about 15 μm in thickness. Also, a mixture of 0.1 part by weight of triamcinolone acetonide as a medicament in a low-dissolving film (layer I), 9.9 parts by weight of propylene glycol, 30 parts by weight of polyvinylpyrrolidone, 60 parts by weight of highly substituted hydroxypropyl cellulose, and 2,000 parts by weight of ethanol was spread on the intestine-soluble film and dried to provide a double layer film having about 115 μm in thickness. Also, a mixture of 0.1 part by weight of triamcinolone acetonide as a medicament in a fast dissolving film (layer II), 9.9 parts by weight of propylene glycol, 60 parts by weight of polyvinylpyrrolidone, 30 parts by weight of lowly substituted hydroxypropyl cellulose, and 500 parts by weight of ethanol was spread on the low-dissolving film and dried to provide three-layer adhesive medical tape (having two medicament-containing layers) of about 130 μm in thickness.

EXAMPLE 8

A mixture of 1.0 parts by weight of diclofenac sodium as a medicament in the slow-dissolving film (layer I), 9.0 parts by weight of propylene glycol, 20 parts by weight of polyvinylpyrrolidone, 70 parts by weight of starch, and 500 parts by weight of water as solvent was spread on the intestine-soluble film as in Example 7 and dried to provide a double layer film and also by following the same procedure as Example 7 except that dichlofenac sodium was used in place of triamcinolone acetonide as the medicament in the fast-dissolving film, a three-layer adhesive medical tape (having two medicament-containing layers) of about 115 μm was produced.

EXAMPLES 9 to 20

According to the preparation method in Example 1 with formulas of table 1, adhesive medical tapes in Examples 9, 10, 11, 15, 17 and 19 were produced. Also, according to the preparation method in Example 7 with formulas of table 1, adhesive medical tapes in Examples 12, 13, 14, 16, 18 and 20 were produced.

Thickness of each Example is 150 μm.

TABLE 1

| Layer | Components | 1 | 2 | 3 | 4 | 5 | 6 | 7 | 8 | 9 | 10 |
|---|---|---|---|---|---|---|---|---|---|---|---|
| Medicament layer (I) | Medicament | | | | | | | | | | |
| | Triamcinolone acetonide | 0.1 | 0.1 | 0.1 | — | — | — | 0.1 | — | 0.5 | 0.5 |
| | Dexamethasone | — | — | — | — | — | — | — | — | — | — |
| | Hydrocortisone acetate | — | — | — | — | — | — | — | — | — | — |
| | Indomethacin | — | — | — | 1.0 | — | — | — | — | — | — |
| | Diclofenac sodium | — | — | — | — | 1.0 | 1.0 | — | 1.0 | — | — |
| | Film forming material | | | | | | | | | | |
| | PVP | 50 | 50 | 50 | 50 | — | — | 30 | 20 | 30 | 30 |
| | HPC-H | 20 | — | — | 20 | — | — | 60 | — | — | 30 |
| | HPC-L | 20 | — | — | 20 | — | — | — | — | 60 | 30 |
| | Sodium polyacrylate | — | — | — | — | 50 | 50 | — | — | — | — |
| | Starch | — | 40 | — | — | 40 | — | — | 70 | — | — |
| | Gelatin | — | — | 40 | — | — | 40 | — | — | — | — |
| | Softening agent | | | | | | | | | | |
| | Propylene glycol | 9.9 | 9.9 | 9.9 | — | — | — | 9.9 | 9.0 | 9.5 | 9.5 |
| | Glycerin | — | — | — | — | 9.0 | 9.0 | — | — | — | — |
| | Polyethylene glycol 400 | — | — | — | 9.0 | — | — | — | — | — | — |
| | Solvent | | | | | | | | | | |
| | Ethanol | 1000 | 250 | 250 | 1000 | — | — | 2000 | — | 1000 | 1000 |
| | Water | — | 250 | 250 | — | 500 | 500 | — | 500 | — | — |

| Layer | Components | 11 | 12 | 13 | 14 | 15 | 16 | 17 | 18 | 19 | 20 |
|---|---|---|---|---|---|---|---|---|---|---|---|
| Medicament layer (I) | Medicament | | | | | | | | | | |
| | Triamcinolone acetonide | 0.5 | 0.5 | 0.5 | 0.5 | — | — | — | — | — | — |
| | Dexamethasone | — | — | — | — | 0.5 | 0.5 | — | — | — | — |
| | Hydrocortisone acetate | — | — | — | — | — | — | 0.5 | 0.5 | — | — |
| | Indomethacin | — | — | — | — | — | — | — | — | 1.0 | 1.0 |
| | Diclofenac sodium | — | — | — | — | — | — | — | — | — | — |
| | Film forming material | | | | | | | | | | |
| | PVP | 30 | 30 | 30 | 30 | 30 | 30 | 30 | 30 | 30 | 30 |
| | HPC-H | 60 | 30 | 60 | 30 | 60 | 60 | 60 | 60 | 60 | 60 |
| | HPC-L | — | 30 | — | 30 | — | — | — | — | — | — |
| | Sodium polyacrylate | — | — | — | — | — | — | — | — | — | — |
| | Starch | — | — | — | — | — | — | — | — | — | — |
| | Gelatin | — | — | — | — | — | — | — | — | — | — |
| | Softening agent | | | | | | | | | | |
| | Propylene glycol | 9.5 | 9.5 | 9.5 | 9.5 | 9.5 | 9.5 | 9.5 | 9.5 | 9.5 | 9.5 |
| | Glycerin | — | — | — | — | — | — | — | — | — | — |
| | Polyethylene glycol 400 | — | — | — | — | — | — | — | — | — | — |
| | Solvent | | | | | | | | | | |
| | Ethanol | 1000 | 1000 | 1000 | 1000 | 1000 | 1000 | 1000 | 1000 | 1000 | 1000 |
| | Water | — | — | — | — | — | — | — | — | — | — |

TABLE 1-continued

| Layer | Components | \_\_\_Example No.\_\_\_ | | | | | | | | | |
|---|---|---|---|---|---|---|---|---|---|---|---|
| | | 1 | 2 | 3 | 4 | 5 | 6 | 7 | 8 | 9 | 10 |
| Medicament layer (II) | Medicament | | | | | | | | | | |
| | Triamcinolone acetonide | | | | | | | 0.1 | — | | |
| | Dexamethasone | | | | | | | — | — | | |
| | Hydrocortisone acetate | | | | | | | — | — | | |
| | Indomethacin | | | | | | | — | — | | |
| | Diclofenac sodium | | | | | | | — | 1.0 | | |
| | Film forming material | | | | | | | | | | |
| | PVP | | | | | | | 60 | 60 | | |
| | HPC-H | | | | | | | — | — | | |
| | HPC-L | | | | | | | 30 | 30 | | |
| | Softening agent | | | | | | | | | | |
| | Propylene glycol | | | | | | | 9.9 | 9.0 | | |
| | Solvent | | | | | | | | | | |
| | Ethanole | | | | | | | 500 | 500 | | |
| Support layer | Intestine-soluble polymer | | | | | | | | | | |
| | HPMCP | 90 | — | — | 90 | — | — | 90 | 90 | 90 | 90 |
| | CAP | — | 90 | — | — | — | — | — | — | — | — |
| | CMEC | — | — | 90 | — | 90 | 90 | — | — | — | — |
| | Softening agent | | | | | | | | | | |
| | Propylene glycol | — | — | — | 10 | — | — | — | — | 10 | 10 |
| | Triacetin | 10 | 10 | 10 | — | 10 | 10 | 10 | 10 | — | — |
| | Solvent | | | | | | | | | | |
| | Ethanol | 250 | 250 | 250 | 250 | 250 | 250 | 250 | 250 | 250 | 250 |
| | Methylene chloride | 250 | 250 | 250 | 250 | 250 | 250 | 250 | 250 | 250 | 250 |

| Layer | Components | \_\_\_Example No.\_\_\_ | | | | | | | | | |
|---|---|---|---|---|---|---|---|---|---|---|---|
| | | 11 | 12 | 13 | 14 | 15 | 16 | 17 | 18 | 19 | 20 |
| Medicament layer (II) | Medicament | | | | | | | | | | |
| | Triamcinolone acetonide | | 0.5 | 0.5 | 2.0 | — | | — | | | — |
| | Dexamethasone | | — | — | — | 0.5 | | — | | | — |
| | Hydrocortisone acetate | | — | — | — | — | | 0.5 | | | — |
| | Indomethacin | | — | — | — | — | | — | | | 1.0 |
| | Diclofenac sodium | | — | — | — | — | | — | | | — |
| | Film forming material | | | | | | | | | | |
| | PVP | | 30 | 30 | 30 | 30 | | 30 | | | 30 |
| | HPC-H | | — | — | 30 | — | | — | | | — |
| | HPC-L | | 60 | 60 | 30 | 60 | | 60 | | | 60 |
| | Softening agent | | | | | | | | | | |
| | Propylene glycol | | 9.5 | 9.5 | 8.0 | 9.5 | | 9.5 | | | 9.0 |
| | Solvent | | | | | | | | | | |
| | Ethanole | | 500 | 500 | 500 | 500 | | 500 | | | 500 |
| Support layer | Intestine-soluble polymer | | | | | | | | | | |
| | HPMCP | 90 | 90 | 90 | 90 | 90 | 90 | 90 | 90 | 90 | 90 |
| | CAP | — | — | — | — | — | — | — | — | — | — |
| | CMEC | — | — | — | — | — | — | — | — | — | — |
| | Softening agent | | | | | | | | | | |
| | Propylene glycol | 10 | 10 | 10 | 10 | 10 | 10 | 10 | 10 | 10 | 10 |
| | Triacetin | — | — | — | — | — | — | — | — | — | — |
| | Solvent | | | | | | | | | | |
| | Ethanol | 250 | 250 | 250 | 250 | 250 | 250 | 250 | 250 | 250 | 250 |
| | Methylene chloride | 250 | 250 | 250 | 250 | 250 | 250 | 250 | 250 | 250 | 250 |

Each numeral shows parts by weight

What is claimed is:

1. An adhesive medical tape for oral mucosa comprising a support layer consisting essentially of an intestine-soluble polymer and at least two medicament-containing layers consisting essentially of a water-soluble polymer containing a steroid or non-steroid antiphlogistic and analgesic agent wherein the steroid medicament is selected from the groups consisting of triamcinolone acetonide fluocinolone betamethasone dexamethasone acetate, hydrocortisone acetate, prednisolone, prednisolone valerate and beclomethasone propionate, and wherein the non-steroid medicament is selected from the group consisting of indomethacin diclofenac sodium, bufexamac, ibuprofenpiconol, butyl flufenamate and bendazac, and whereas the water soluble polymer is selected from the group consisting of polyvinylpyrrolidone, polyvinyl alcohol, sodium polyacrylate, sodium algiante, sodium carboxymethyl cellulose, methylcellulose, hydroxypropyl cellulose, carboxyvinyl polymer gelatin, xanthen gum karaya gum, starch, agar-agar and mixture thereof wherein the intestine-soluble polymer is selected from the group consisting of hydroxypropyl cellulose phthalate, cellulose, poly(methacrylic acid, methylmethacrylate) and a mixture thereof.

2. The adhesive medical tape as claimed in claim 1, wherein the steroid medicament is contained in an amount of 0.05 to 1.0 part by weight.

3. The adhesive medical tape as claimed in claim 1, wherein the non-steroid medicament is contained in an amount of 0.5 to 5.0 parts by weight.

4. The adhesive medical tape as claimed in claim 1, wherein the thickness of the support layer is 2-20 μm and that of the medicament-containing layers is 20-300 μm.

5. The adhesive medical tape as claimed in claim 1, wherein the medicament-containing layer adhering to a mucous membrane consists of a fast dissolving layer and the other layer which is not adhering to a mucous membrane consists of a slow dissolving layer.

6. The adhesive medical tape as claimed in claim 1, wherein the medicament-containing layer adhering to a mucous membrane consists of a high concentration of medicament layer and the other layer which is not adhering to a mucous membrane consists of a low concentration of medicament layer.

* * * * *

UNITED STATES PATENT AND TRADEMARK OFFICE
CERTIFICATE OF CORRECTION

PATENT NO. : 4,765,983

DATED : August 23, 1988

INVENTOR(S) : Hitoshi Takayanagi, et al

It is certified that error appears in the above-identified patent and that said Letters Patent is hereby corrected as shown below:

Column 2, line 52: "be clomethasone" should be --beclomethasone--

Column 9, line 58: after "acetonide" insert a comma; delete "betamethasone" and replace with --acetonide, dexamethasone,--.

Column 9, line 60: after "valerate" insert a comma; then insert --betamethasone valerate--.

Column 10, line 52: "xanthen" should be --xanthane--.

Column 10, line 54: "hydroxypropyl" should be --hydroxypropylmethyl--.

Column 10, line 55: after "phthalate," insert --cellulose acetate phthalate, carboxymethyl--.

Signed and Sealed this

Seventh Day of March, 1989

Attest:

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,765,983

DATED : August 23, 1988

INVENTOR(S) : Hitoshi Takayanagi, et al.

It is certified that error appears in the above-identified patent and that said Letters Patent is hereby corrected as shown below:

On the Title Page, Item [73], the correct Assignees should be
--Yamanouchi Trading Co., Ltd.; Kyukyu Pharmaceutical Co., Ltd., and Squibb Japan, Inc.--.

Column 2, line 52: "be clomethasone" should be --beclomethasone--.

Column 9, line 58: after "acetonide" insert a comma; delete "betamethasone" and replace with --acetonide, dexamethasone,--.

Column 9, line 60: after "valerate" insert a comma; then insert --betamethasone valerate--.

Column 10, line 52: "xanthen" should be --xanthane--.

Column 10, line 54: "hydroxypropyl" should be --hydroxypropylmethyl--.

Column 10, line 55: after "phthalate," insert --cellulose acetate phthalate, carboxymethylethyl--.

This certificate supersedes Certificate of Correction issued March 7, 1989.

Signed and Sealed this

Eighth Day of August, 1989

Attest:

DONALD J. QUIGG

Attesting Officer

Commissioner of Patents and Trademarks